United States Patent [19]

Waldron

[11] 4,378,212

[45] Mar. 29, 1983

[54] ROTARY DRIVING APPARATUS HAVING A COLLET WITH A MAGNETIC LATCHING MECHANISM

[75] Inventor: Stephen H. Waldron, Camarillo, Calif.

[73] Assignee: Spire Medical Inc., Ventura, Calif.

[21] Appl. No.: 304,061

[22] Filed: Sep. 21, 1981

[51] Int. Cl.³ .............................................. A61C 00/00
[52] U.S. Cl. .................................... 433/128; 279/1 M; 279/93
[58] Field of Search ......................... 279/1 M, 93, 94; 81/3 R; 29/270; 433/128

[56] References Cited

U.S. PATENT DOCUMENTS

| 1,824,509 | 9/1931 | Snader | 279/93 |
| 2,051,718 | 8/1936 | Kalfenbach et al. | 433/128 |
| 2,550,775 | 5/1957 | Clark | 279/1 M |

*Primary Examiner*—Robert Peshock
*Attorney, Agent, or Firm*—Daniel J. Meaney, Jr.

[57] ABSTRACT

A rotary driving apparatus having a collet housing defining a passageway which is adapted to receive, engage and rotate a bur having one end thereof which terminates in a notched bur key formed of a magnetizable material having a driving shaft having a first end and a second end which is rotatably supported in a collet housng with the first end of the driving shaft operatively coupled to and rotated by a rotary driving motor and with the second end of the driving shaft positioned within the collet housing passageway and being adapted to receive the bur and to engage and rotate the end of the bur which terminates in a notched bur key formed of a magnetizable material and wherein the second end of the driving shaft includes a cylindrically shaped housing defining a capture cavity and side walls which form a slotted opening which communicates with the capture cavity and with the collet housing passageway to receive and pass the notched bur key end of a bur transported within the collet passageway and to position the notched bur key end adjacent the slotted opening such that rotation of the driving shaft urges the side walls forming the slotted opening into removable driving engagement with the notched bur key end and wherein a magnet is located within the capture cavity for establishing a magnetic field which encloses the slotted opening and which has a flux density of sufficient magnitude to magnetically couple the magnetizable material forming the notched bur key end to removably hold the notched bur key end of the bur within the slotted opening independent of the driving engagement between the side walls forming the slotted opening and the notch of the notched bur key end is shown.

14 Claims, 11 Drawing Figures

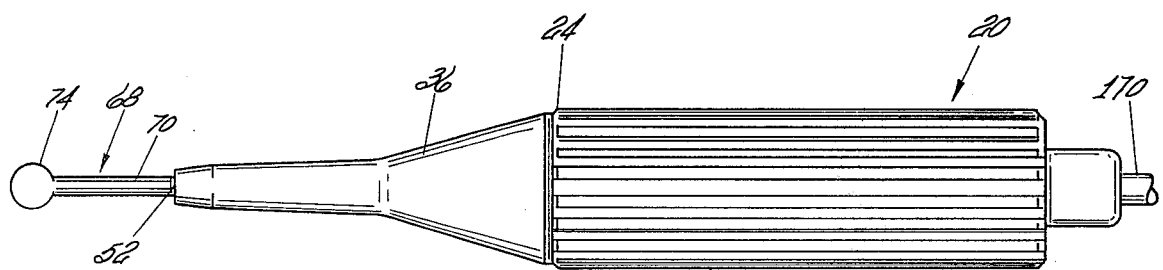
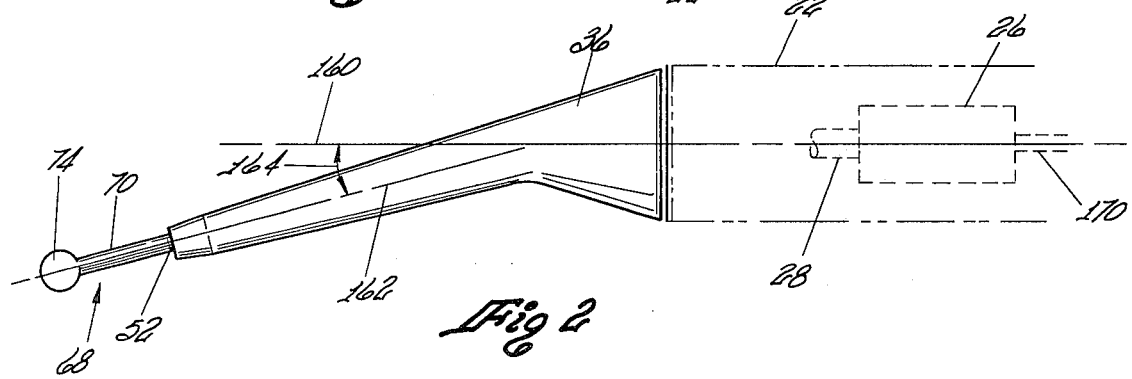
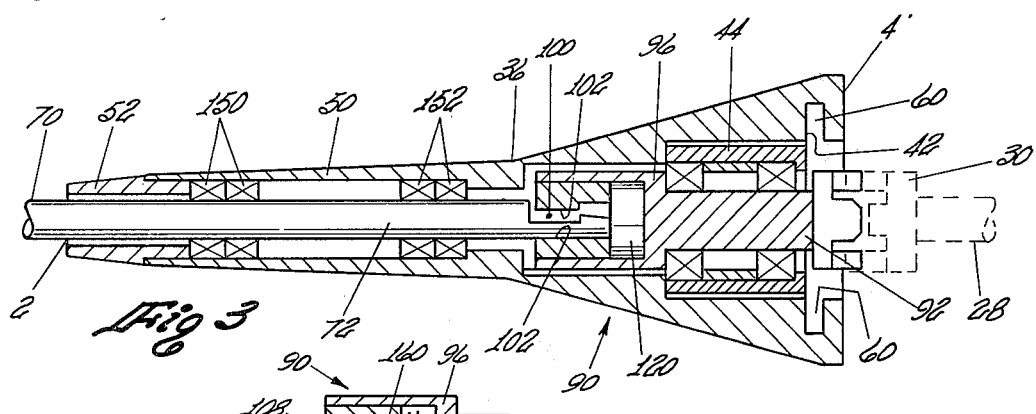
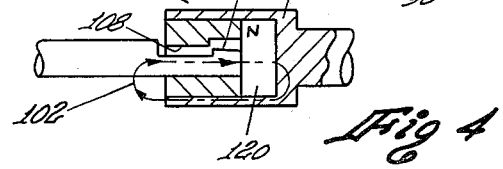
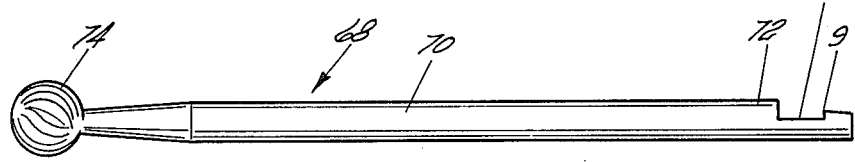

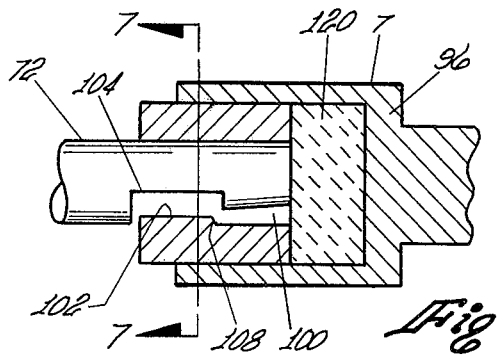
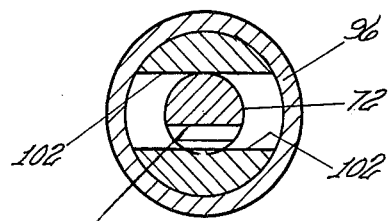
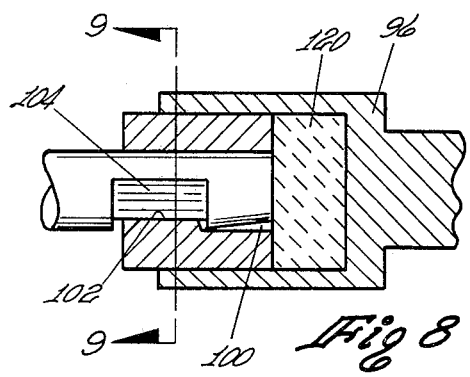
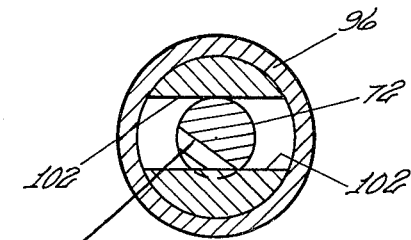
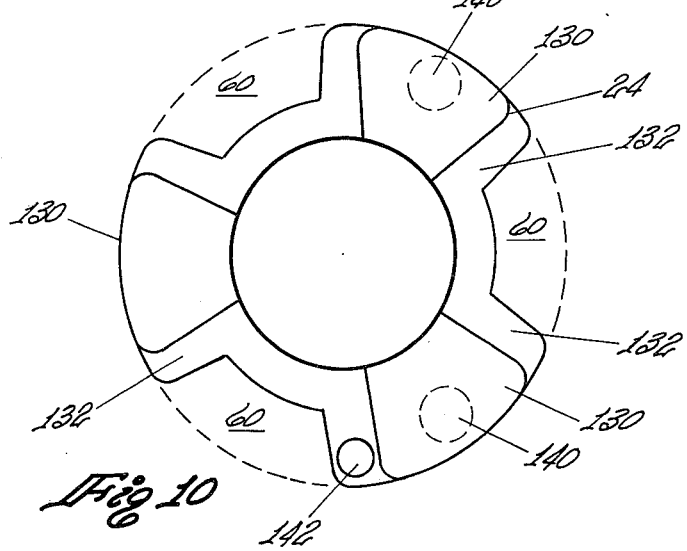
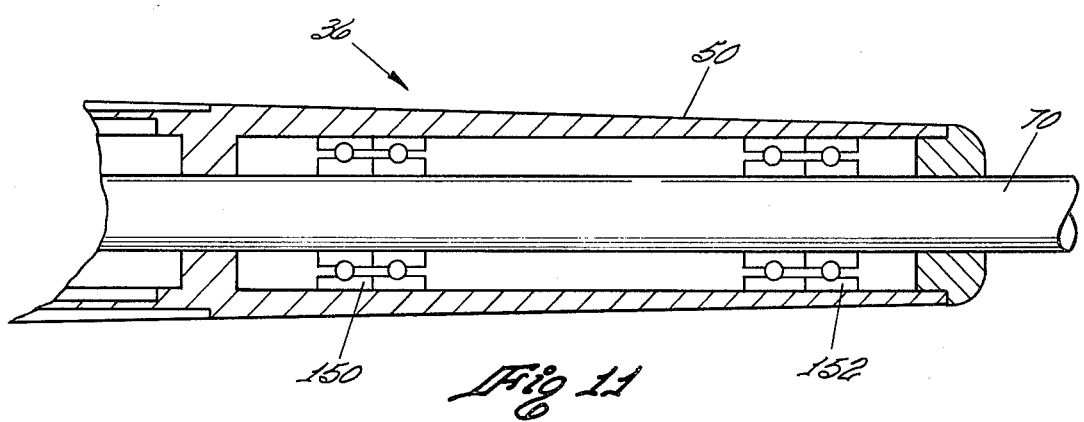

ROTARY DRIVING APPARATUS HAVING A COLLET WITH A MAGNETIC LATCHING MECHANISM

BACKGROUND OF THE INVENTION

1. Field of the Invention

This invention relates to a rotary driving apparatus having a collet housing which defines a passageway which is adapted to receive, engage and rotate a bur having one end thereof which terminates in a notched bur key formed of a magnetizable material and more specifically to a high speed rotary drill having a collet housing which contains a bearing and which is adapted to have a bur having a notched bur key formed of a magnetizable material at one end thereof slidably inserted into the collet housing wherein the notched bur key is inserted into a capture cavity and removably held in place by a magnet wherein the bur can be easily removed with a slight twist and then withdrawn from the collet housing.

2. Description of the Prior Art

Rotary surgical drills with detachable hand pieces and removable burs are well known in the art. Typical of such known devices are set forth in U.S. Pat. No. 4,055,185; U.S. Pat. No. 3,867,943; U.S. Pat. No. 3,835,858; U.S. Pat. No. 3,709,630; U.S. Pat. No. 3,614,824; U.S. Pat. No. 3,010,193; U.S. Pat. No. 1,905,851; U.S. Pat. No. 3,173,417; U.S. Pat. No. 1,076,971; U.S. Pat. No. 3,128,079; U.S. Pat. No. 3,472,323; and U.S. Pat. No. 3,384,085.

Specifically, U.S. Pat. No. 4,055,185 wherein the inventor is the same inventor of the instant application, the rotary drill adapted for use in surgery has a rotary bur assembly which includes a driven gear and axially aligned spaced bearings. The rotary bur assembly is held within the collet housing by a latching mechanism.

U.S. Pat. No. 3,867,943 discloses a surgical drill with a detachable hand piece wherein the detachable hand piece includes a driven shaft and a claw attached thereto which is adapted to operatively mate with the drive clutch.

U.S. Pat. No. 3,835,858 discloses an improved surgical air drill wherein both the bur and the hand piece are removable and the hand piece is interchangeable with the rotary driving means. A severable coupling between the motor and the hand piece permits interchanging of the hand pieces, which hand pieces include the bur being inserted therein. The bur and its shank is secured to the hand piece shaft in a semi-permanent manner.

It is also known in the art to utilize a magnet or magnetic holding means in a wide variety of apparatus, tools and the like. Typical of such devices are those disclosed in U.S. Pat. No. 4,161,943; U.S. Pat. No. 3,320,563; U.S. Pat. No. 2,718,806; U.S. Pat. No. 2,808,862; U.S. Pat. No. 1,956,634; U.S. Pat. No. 3,257,876; and U.S. Pat. No. 3,253,626.

U.S. Pat. No. 4,161,943 discloses a needle implanting apparatus for implanting magnetized or magnetizable needles and includes a permanent magnet to hold the magnetized needles in a predetermined position for implantation.

U.S. Pat. No. 3,320,563 discloses a magnetic driving implement with cup-shaped magnetic portion for greater holding strength which is adapted to hold bolts in position. The shank of the socket wrench includes a cup-shaped member formed of magnetic material.

U.S. Pat. No. 2,718,806 discloses a magnetic driving tool having a socket which includes a magnet.

U.S. Pat. No. 4,157,714 discloses a portable surgical wire inserting instrument which is adapted to utilize sterile wire pack having a flat end which is adapted to be mounted within the chuck of the wire inserting instrument.

SUMMARY OF THE INVENTION

This invention relates to a new, novel and unique rotary driving apparatus having a collet housing which defines a passageway which is adapted to receive, engage and rotate a bur having one end thereof which terminates in a notched bur key formed of a magnetizable material. In the preferred embodiment, the rotary driving apparatus comprises a driving means having a first end and a second end wherein the driving means is rotatably supported in the collet housing. The first end of the driving means is adapted to be operatively coupled to and rotated by the rotary driving means. The second end of the driving means is positioned within the collet housing passageway and is adapted to receive the bur and is adapted to engage and rotate the end of the bur which terminates in a notched bur key formed of a magnetizable material. The second end of the driving means further includes means defining a capture cavity and side walls which form a slotted opening which communicates with the capture cavity and the collet housing passageway. The slotted opening is adapted to receive and pass the notched bur key end of the bur transported within the collet passageway and to position the notched bur key and adjacent the slotted opening such that the rotation of the driving means urges the side walls forming the slotted opening into removable driving engagement with the notched bur key end. The second end of the driving means further includes magnetic means located within the capture cavity for establishing a magnetic field which encloses the slotted opening and which has a flux density of sufficient magnitude to magnetically couple the magnetizable material forming the notched bur key end to removably hold the notched bur key end of the bur within the slotted opening independent of the driving engagement between the side walls forming the slotted opening and the notch of the notched bur key end.

In the known prior art devices, the bur typically includes a bur rotating assembly which includes bearings, a sleeve and a driven coupling element. Also, it is known in the art to utilize a hand piece having the bur mounted semi-permanently therein in order to obtain true axial alignment of the bur within the collet housing. If a surgeon desires to change burs, the entire assembly must be changed. The cost of fabricating the bur assemblies or hand piece having the bur are substantial. Also, it is necessary to utilize latches or other fastening means and the same must be connected in order to remove and replace the bur assemblies onto a driven motor.

Although prior art devices disclose the use of a magnet as part of a tool, none of the prior art devices disclose or suggest the use of a magnetic holding means in combination with a slotted capture cavity as a means for receiving a notched bur key formed of a magnetizable material and located at one end of a bur.

One advantage of the present invention is that a bur can be easily inserted into the rotary drill by sliding the notched bur key end thereof through the passageway defined in the collet housing past the slotted opening into the capture cavity such that the bur is removably in driving engagement with the driving shaft.

Another advantage of the present invention is that a driving force is urged on the notched bur key end formed of the magnetizable material by the side walls defining the slotted opening such that a driving force supplied to the notched bur key end during use thereof.

A further advantage of the present invention is that a surgeon, during surgery, can stop the rotary driving apparatus and by merely applying a small force onto the bur can remove the bur and replace the same with another bur having a notched bur key end formed of a magnetizable material which then can be slid into the passageway of the collet housing and into the capture cavity wherein the notched bur key formed of the magnetizable material is held in position independent of a driving force by a magnetic field applied thereto through a magnet.

A yet further advantage of the present invention is that the rotary driving means may be an electric motor which is actuated through a power packed and foot control system so that a surgeon is provided with the ease of starting, stopping and reversing the rotary driving means which permits the surgeon to utilize the drill with great ease during surgery including the ease of removing and replacing burs into the surgical drill during surgery.

BRIEF DESCRIPTION OF THE DRAWING

The foregoing and other advantages of this invention will be apparent from the following description of the preferred embodiment of the invention when considered with the illustrations and the accompanying drawing which includes the following figures:

FIG. 1 is a top plan view of a rotary driving apparatus showing the central housing, collet housing and bur;

FIG. 2 is a front plan view of a collet housing and bur having the central housing shown in dashed lines;

FIG. 3 is a sectional view of the collet housing showing the bur and the end thereof which terminates in a notched bur key and its relationship with the driving shaft;

FIG. 4 is pictoral representation partially in cross-section showing the relationship between the driving means, the means defining a capture cavity and magnetic means;

FIG. 5 is a front plan view of a bur and one end thereof which terminates in a notched bur key formed of a magnetizable material;

FIG. 6 is a pictoral representation partially in cross-section showing the relationship between a drive shaft, magnet and segmented circular sections which define the capture cavity and the notched bur key end of a bur in the insert position;

FIG. 7 is a cross-sectional view taken along section lines 7—7 of FIG. 6;

FIG. 8 is pictoral representation partially in cross-section illustrating the elements of FIG. 6 wherein the notched bur key end and side walls defining the slotted opening are in driving engagement;

FIG. 9 is a sectional view taken along section lines 9—9 of FIG. 8;

FIG. 10 is a pictoral representation of the relationship between the interconnecting lugs and the segmented shaped openings which are utilized to define the first and second interconnecting members; and FIG. 11 is a pictoral representation of the collet housing showing the bearing means which includes two spaced bearings to support the shaft of a bur.

DESCRIPTION OF THE PREFERRED EMBODIMENT

FIG. 1 illustrates the rotary driving apparatus shown generally as 20 which includes an elongated housing 22 having a central cavity and an opening at one end thereof which communicates with the central cavity. The elongated housing 20 includes means for defining a first interconnecting member 24 located adjacent the opening.

A motor, shown by dashed rectangle 26, has an output shaft shown by dashed shaft 28 extending through the opening located at the one end of the elongated housing 22. A first drive connecting element shown by dashed "U" shaped member 30 in FIG. 3 is operatively coupled to the output shaft 28 adjacent the opening.

A collet housing 36, which is illustrated in FIGS. 2 and 3, has a first portion 40 which includes means defining a first aperture 42 at one end thereof and a hollowed out central area 44 which communicates with the first aperture 42. The collet housing 36 includes a second generally conical shaped portion 50 having a passageway 52 which extends axially from the apex to the base of the conical shaped portion 50. The base of the conical shaped portion 50 is positioned contiguous the first portion 40 with the passageway 52 communicating with the hollowed out area 44. The second interconnecting member 60 which is adjacent the first opening 42 is adapted to cooperate with the first interconnecting members 24 which are located adjacent the first opening such that the elongated housing 22 is releasably secured to the collet housing 36 for securing the elongated housing 22 and the collect housing 36 together to form an integral unit therebetween as illustrated in FIG. 1.

In use, the rotary driving apparatus is adapted to receive and drive a bit 68 having a bit shank 70 which terminates at one end thereof in a bit flange 72. The other end of the bit 68 terminates in a bur of which bur 74 is typical.

In surgery, a surgeon may utilize one or more burs during surgery when performing operations such as for example in removing portions of an ear bone.

Accordingly, it is an important feature of the invention that the bur can be easily inserted and removed during surgery. A surgeon, can easily remove one bur and replace it with an identical or larger bur, depending on the step of the operation. Thus, the bur would have two operating conditions during use; namely, (1) when it is inserted and waiting to be used; and, (2) when it is actually in use and is being driven by the drive shaft.

FIGS. 3 and 4 show in greater detail the construction of the driving means 90 which has a first end 92 and a second end 96. The driving means, which, in the preferred embodiment, is a driving shaft, is rotatably supported in the collet housing 36 with the first end 92 adapted to be operatively coupled to and rotated by the rotary driving means through output shaft 28 and the first drive connecting element 30. The second end 96 of the driving means 90 is positioned within the collet housing passageway 52, namely at the end thereof, and is adapted to receive a bur 68 and is adapted to engage and rotate the end of the bur 72. In the embodiment illustrated in FIGS. 3, 4 and 5, the bur 68 terminates in a notched bur key formed of a magnetizable material. In the preferred embodiment, the drive shaft 96 may be formed of a nonmagnetic material such as, for example, type 303 stainless steel.

The second end 96 of the drive shaft 90 defines a capture cavity 100 which includes side walls 102 which form a slotted opening which communicates with the capture cavity 100 and with the collet housing passageway 52. The slotted opening defined by side walls 102 is adapted to receive and pass the notched bur key end 72 of a bur 68 transported within the collet passageway 52 to position the notched bur key end 72 adjacent the slotted opening defined by side walls 102 such that rotation of the driving means, such as motor 26, urges the sidewalls 102 forming the slotted opening into removable driving engagement with the end of the notched bur key 72.

This is illustrated in detail in FIGS. 6, 7, 8 and 9.

Specifically, FIGS. 6, 7, 8 and 9 show that the notched bur key end 72 has a notched area 104 formed therein which has a lip 106 terminating at the end thereof. Lip 106 is adapted to cooperate with the side walls 102 which define the slot. The elongated slot 104 defines a key way which is adapted to cooperate with the slot 102 to permit the driving engagement to occur between the face 102 and the elongated slot 104 defining the key way.

A magnetic means, such as a magnet 120 is located within the capture cavity 100 for establishing a magnetic field which encloses the slotted opening and which has a flux density of sufficient magnitude to magnetically couple the magnetizable material forming the notched bur key end 72 to removably hold the notched bur key end 72 of bur 68 within the slotted opening defined by sidewalls 102 independent of the driving engagement between the sidewalls 102 forming the slotted opening and notch 104 of the notched bur key end 72.

FIGS. 7 and 9 illustrate that the slotted member is rectangular in shape. Also, as illustrated in FIGS. 7 and 9, both of the notched bur key 72 and the aperture cavity has a generally cross-sectional area.

FIG. 10 illustrates that the first interconnecting member 24 is formed of a plurality of coplanar arcuate shaped connecting lugs 130 and wherein the second interconnecting member is a plurality of coplanar slotted cavities separated by segmented shaped openings 132. The segmented shaped openings communicate with the coplanar slotted cavities 60 (FIG. 4) which define the second interconnecting means. As illustrated in FIG. 10, rotation of the central housing 24 and the collet housing 36 relative to each other results in the connecting lugs 130 moving from the segmented shaped openings 132 into the slotted cavities 60. A recess area 140 located in the connecting lugs is adapted to cooperate with a ball 142 to form an interlocking ball recess means for insuring that the central housing 22 and the collet housing 36 will remain together as an integral unit.

FIG. 11 illustrates the conical shaped portion 50 of the collet housing 36 to support the shaft 70 of a bur.

In the embodiment illustrated in FIG. 11, the collet housing 50 includes a bearing means having two spaced bearings 150 and 152 which are positioned to rotatably support the bit shaft 70 at two spaced locations. The bearings 150 and 152 have sufficient geometrical cross-sectional area dimension to permit the bit flange 70 to pass therethrough and to enter into engagement with the capture cavity 100.

Referring to FIG. 2, the central passageway located within the center of the central housing 22 has an axis illustrated by dashed line 160. The hollowed out central area within the collet housing 36 has an axis illustrated by line 162.

As illustrated in FIG. 1, the axis of the hollowed out central area 160 and the axis of the hollowed out central area within collet housing 36 can be mounted in either axial alignment or at an acute angle. In FIG. 2, the selected acute angle can range from about 10° to about 30°. This is shown by the angle depicted by arrow 164. In the preferred embodiment, the selected acute angle is about 17°.

The rotary driving apparatus of the present invention has utility as a high speed drill used by surgeons for otological auto-neurological surgery. The entire system can comprise an electric motor which runs as 24,000 revolutions per minute. The two collet housings, which are sometimes referred to as hand pieces, can either be straight or angled. A cord, illustrated by cord 170 in FIG. 2, may be utilized if the motor is an electric motor. If the motor is an air driven motor or a gas driven motor, cord 170 may be an appropriate air or gas supply line.

In the preferred embodiment, the motor is an electric motor and is connected to an electrical source through a foot control. The motor 26 may be operated either by a battery or a 150 volt current can be used to power the system.

What is claimed is:

1. A rotary driving apparatus having a collet housing passageway which is adapted to receive, engage and selectively rotate in one of a clockwise and counterclockwise direction a bur having one end thereof which terminates in a notched bur key end formed of a magnetizable material and having a lip extending from the notch comprising a driving means having a first end and a second end, said driving means being rotatable supported in the collet housing passageway with the first end of the driving means adapted to be operatively coupled to and rotated by a rotary driving means and with the second end of the driving means positioned within the collet housing passageway and being adapted to receive a bur which terminates in a notched bur key end formed of a magnetizable material, said second end of said driving means including means defining interior to the collet housing passageway a capture cavity and side walls for forming a slotted opening which communicates with the capture cavity, said slotted opening being adapted to receive and pass the notched bur key end of a said bur transported through the collet passageway and to pass the lip through the slotted opening and into the capture cavity positioning the notch of a said notched bur key end contiguous the slotted opening such that rotation of the driving means in one of a clockwise and counterclockwise direction urges the side walls forming the slotted opening into removeable driving engagement with the contiguous notch of a said notched bur key end; and magnetic means located within said capture cavity for establishing a magnetic field which encloses said slotted opening and which has a flux density of sufficient magnitude to magnetically couple the magnetizable material forming a said notched bur key end to urge the lip of a said notched bur key passed said slotted opening and being adapted to removeably hold a said notched bur key end of a said bur within the slotted opening independent of the driving engagement between the side walls forming the slotted opening and the notch of a said notched bur key end.

2. The rotary driving apparatus of claim 1 wherein the driving means is a driving shaft having a first end which is adapted to be coupled to a drive motor through a flexible driving member and a second end which has a rectangular shaped slotted opening having a width which is adapted to pass the notched bur key end.

3. The rotary driving apparatus of claim 1 wherein the notched bur key end of a said bit has a circular cross-sectional area and an elongated slot forming the notch and wherein the capture cavity has a generally circular cross-sectional area and the slotted opening has a generally rectangular shaped cross-sectional area.

4. The rotary driving apparatus of claim 1 wherein said driving means comprises
 a drive shaft having a shank formed of a non-magnetic material which terminates at one end thereof in a removeable driving element and which terminates at the other end thereof in a cylindrical shaped cavity having a bur key receiving opening; and wherein said magnetic means includes
 a magnetic means located within the cylindrical shaped cavity of said drive shaft; and wherein said side walls which define the slotted opening are formed of semi-circular shaped members, each of which has a planar surface and each of which is positioned within the bur key receiving opening with the planar surfaces positioned in a spaced parallel opposite relationship to define a slot having a geometrical dimension to receive and pass the notched bur key end of the bur and to define a slotted key which is adapted to removeably engage the notched bur key end to rotate the same.

5. A rotary driving apparatus adapted to receive and drive a bit having a bit shank which terminates at one end thereof in a bit flange formed of magnetizable material and having a flat planar surface formed thereon, said rotary driving apparatus comprising
 an elongated housing having a central cavity and an opening at one end thereof which communicates with the central cavity, said elongated housing including means for defining a first interconnecting member located adjacent the opening;
 a motor having an output shaft positioned within the elongated housing with the output shaft extending through the opening located at said one end of said elongated housing;
 a first drive connecting element operatively coupled to said output shaft adjacent said opening;
 a collet housing having a first portion which includes means defining a first aperture at one end thereof and a hollowed-out central area which communicates with the first aperture, said collet housing including a second generally conical shaped portion having a passageway which extends axially from the apex to the base of the conical shaped portion and with the base of the conical shaped portion positioned contiguous said first portion and with said passageway communicating with the hallowed-out central area, said first aperfure having a second interconnecting member adjacent the first opening which is adapted to cooperate with the first interconnecting member on said elongated housing for releasable securing said elongated housing to said collet housing to form an integral unit therebetween; and
 a driving means having a first end and a second end, said driving means being rotatably supported in said collet housing with the first end of the driving means having a second drive connecting element operatively coupled thereto which is adapted to make a separatably driving engagement with said first drive connecting element and with the second end of the driving means positioned within the collet housing passageway to receive the bit and to engage and rotate the end thereof which terminates in the bit flange formed of a magnetizable material, said second end of said driving means including
 means defining a capture cavity and side walls which form a slotted opening which communicates with the capture cavity and with the collet housing passageway, said slotted opening being adapted to receive and pass the bit flange of the end of a bit transported within the collet passageway and to position the bit flange adjacent the slotted opening such that rotation of the driving means urges the side walls forming the slotted opening into removeable driving engagement with the flange end of the bit; and
 magnetic means for establishing a magnetic field which encloses said slotted opening and which has a flux density of sufficient magnitude to magnetically urge the flange end of a said bit through the slotted opening and to couple the magnetic material forming said bit flange to removeably hold the bit flange of a said bit within the slotted opening independent of the driving engagement between the side walls forming the slotted opening and the flat planar surface of the bit flange of a said bit.

6. The rotary driving apparatus of claim 5 wherein said passageway is in axial alignment with the axis of the hollowed-out central area and with the axis of the central cavity.

7. The rotary driving apparatus of claim 5 wherein said central passageway is located at a selected acute angle with the axially aligned axes of the hollowed-out central area and central cavity.

8. The rotary driving apparatus of claim 7 wherein said selected acute angle is about 10° to about 30°.

9. The rotary driving apparatus of claim 8 wherein the selected acute angle is about 17°.

10. The rotary driving apparatus of claim 5 wherein said first interconnecting member is a plurality of co-planar arcuate shaped segments forming connecting lugs and wherein said second interconnecting member is a plurality of co-planar slotted cavities separated by segmented shaped openings which communicate with the co-planar slotted cavities and wherein the geometrical shape of the segmented shaped openings is adapted to receive the connecting lugs such that the aperture of the elongated housing can be positioned into the segmented shaped cavities and wherein rotation of the elongated housing relative to the collet housing remove the connecting lugs from the segmented shaped cavities into the slotted cavities locking the elongated housing and collet housing together into an integral unit.

11. The rotary driving apparatus of claim 10 wherein said first driving member includes a "U" shaped member and said second drive member includes a "U" shaped member wherein the legs of each "U" shaped member are adapted to slide into each other to form a removable driving universal joint therebetween.

12. The rotary driving apparatus of claim 11 wherein said drive shaft is formed of a nonmagnetic material.

13. The rotary driving apparatus of claim 11 wherein the drive shaft nonmagnetic material is formed of type 303 stainless steel.

14. The rotary driving apparatus of claim 5 wherein said collet housing includes a bearing means having two spaced bearings which are positioned to rotatably support the bit shaft at two spaced locations and have sufficient geometrical cross-sectional area dimension to permit the bit flange to pass therethrough and into engagement with the capture cavity.

* * * * *